US012485209B2

(12) United States Patent
Horschke et al.

(10) Patent No.: US 12,485,209 B2
(45) Date of Patent: Dec. 2, 2025

(54) MEDICAL APPLIANCE FOR EXTRACORPOREAL BLOOD TREATMENT

(71) Applicant: B. Braun Avitum AG, Melsungen (DE)

(72) Inventors: Sebastian Horschke, Hessisch Lichtenau (DE); Marco Jakobi, Uder (DE)

(73) Assignee: B. Braun Avitum AG, Melsungen (DE)

( * ) Notice: Subject to any disclaimer, the term of this patent is extended or adjusted under 35 U.S.C. 154(b) by 368 days.

(21) Appl. No.: 18/007,842

(22) PCT Filed: May 28, 2021

(86) PCT No.: PCT/EP2021/064379
§ 371 (c)(1),
(2) Date: Dec. 2, 2022

(87) PCT Pub. No.: WO2021/244973
PCT Pub. Date: Dec. 9, 2021

(65) Prior Publication Data

US 2023/0347030 A1 Nov. 2, 2023

(30) Foreign Application Priority Data

Jun. 3, 2020 (DE) ..................... 10 2020 206 873.9

(51) Int. Cl.
*A61M 1/16* (2006.01)
*A61M 1/36* (2006.01)

(52) U.S. Cl.
CPC ........ *A61M 1/1621* (2014.02); *A61M 1/1645* (2014.02); *A61M 1/3641* (2014.02); *A61M 2205/0216* (2013.01)

(58) Field of Classification Search
CPC ........ A61M 1/36222; A61M 1/362223; A61M 1/362227; E05D 11/1064;
(Continued)

(56) References Cited

U.S. PATENT DOCUMENTS 4,658,547 A * 4/1987 Oboza ................. E05D 11/1078 16/337
5,928,177 A * 7/1999 Brugger .............. A61M 60/279 604/6.11

(Continued)

FOREIGN PATENT DOCUMENTS

DE 2532484 A1 2/1977
DE 202011004678 U1 7/2011

(Continued)

OTHER PUBLICATIONS

Search Report received in International Application No. PCT/EP2021/064379 dated Sep. 8, 2021, with translation, 6 pages.

(Continued)

*Primary Examiner* — Nicholas J. Weiss
*Assistant Examiner* — Seth Han
(74) *Attorney, Agent, or Firm* — Christopher A. Rothe; CM Law

(57) ABSTRACT

A medical appliance for use in extracorporeal blood treatment. The appliance includes a housing component, a cover and a pivot bearing arrangement by which the cover is mounted on the housing component. The cover is pivotable between a covering position, in which the housing component is covered, and a exposure position, in which the housing component is exposed. The pivot bearing arrangement has pivot bearings, each having a bearing element and a bearing element receptacle. The cover can move linearly relative to the housing component between a dismounting position, in which at least one of the bearing elements is disengaged from a bearing element receptacle, and a bearing position, in which both bearing elements engage the bearing element receptacles. The cover is mounted resiliently and elastically preloaded relative to the housing component by a spring arrangement.

10 Claims, 7 Drawing Sheets

Figure 1:
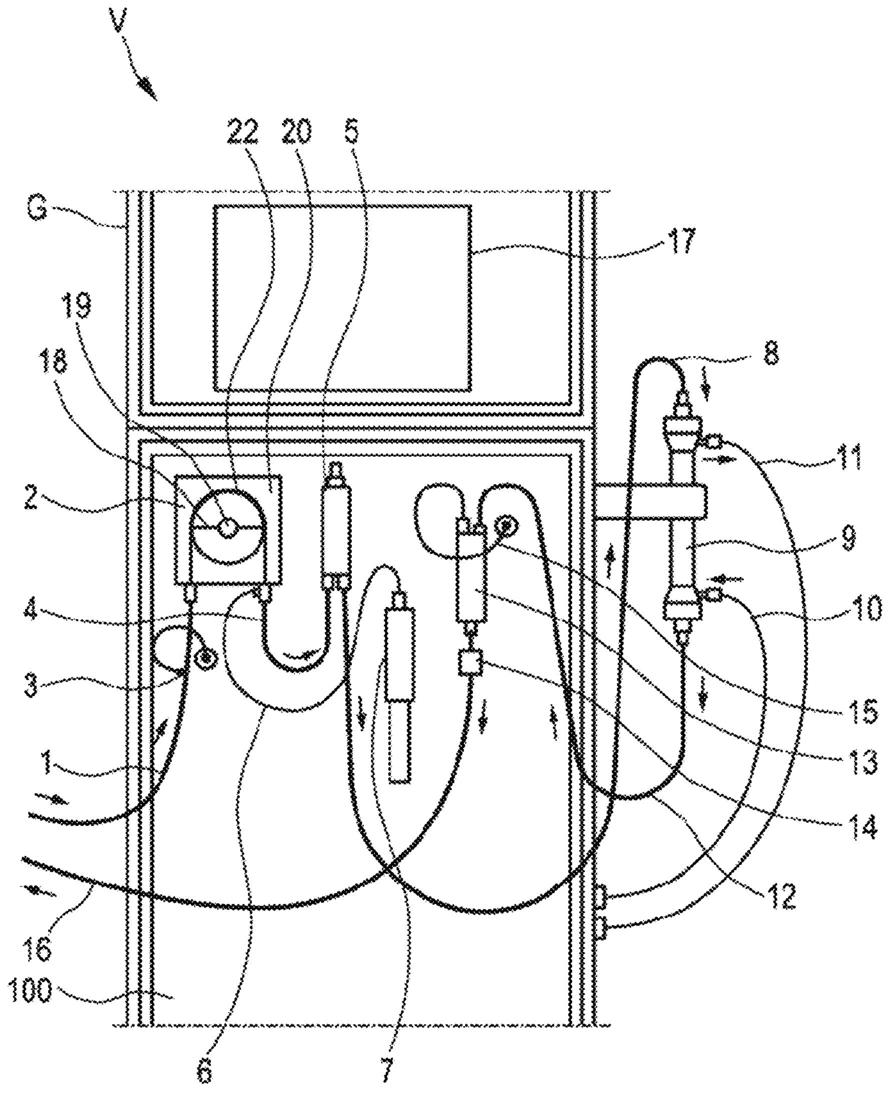

(58) Field of Classification Search
CPC ........... E05D 2007/1027; E05D 11/105; E05D 7/1005; E05D 7/1011; E05D 2007/1033; E05D 2007/1038; E05D 7/081; E05D 3/00; E05D 3/06; E05D 7/12
See application file for complete search history.

(56) References Cited

U.S. PATENT DOCUMENTS

| | | | | |
|---|---|---|---|---|
| 6,205,616 | B1 * | 3/2001 | Hwang | E05D 7/1011 16/229 |
| 7,062,817 | B2 * | 6/2006 | Lee | E05F 1/1223 16/334 |
| 8,454,553 | B2 * | 6/2013 | Fontanazzi | A61M 1/36225 604/65 |
| 9,415,911 | B2 | 8/2016 | Schaefer | |
| 2002/0029793 | A1 | 3/2002 | Dunn et al. | |
| 2012/0316507 | A1 | 12/2012 | Agard et al. | |
| 2013/0111818 | A1 | 5/2013 | Yagi et al. | |

FOREIGN PATENT DOCUMENTS

| | | | |
|---|---|---|---|
| EP | 2679752 | A1 | 1/2014 |
| KR | 2020110000695 | U | 1/2011 |

OTHER PUBLICATIONS https://www.norelem.de/de/de/Produkte/Produkt [...] Druckbolzen-Stahl.html, Spring plungers with slot and thrust pin, steel | norelem, Feb. 25, 2021, with translation, 5 pages.

* cited by examiner

MEDICAL APPLIANCE FOR EXTRACORPOREAL BLOOD TREATMENT

CROSS-REFERENCE TO RELATED APPLICATIONS

This application is the United States national stage entry of International Application No. PCT/EP2021/064379, filed May 28, 2021, and claims priority to German Application No. 10 2020 206 873.9, filed Jun. 3, 2020. The contents of International Application No. PCT/EP2021/064379 and German Application No. 10 2020 206 873.9 are incorporated by reference herein in their entireties.

FIELD

The invention relates to a medical appliance for extracorporeal blood treatment, having a housing component, a cover and a pivot bearing arrangement by means of which the cover is mounted on the housing component and so as to be pivotable about a pivot axis relative to the housing component, wherein the cover is pivotable at least between a covering position, in which the cover covers the housing component, and a release position, in which the cover releases the housing component, and wherein the pivot bearing arrangement has at least two pivot bearings arranged spaced apart from one another along the pivot axis.

BACKGROUND

A medical appliance of this type is known in the form of a dialysis appliance for extracorporeal blood treatment from EP 2 679 752 A1. The dialysis appliance has a peristaltic pump with a pump housing and a pump cover. The pump cover is mounted on the pump housing by means of a pivot bearing arrangement so as to be pivotable about a pivot axis relative to the pump housing between a covering position and a release position. In the covering position, the pump housing is covered by means of the pump cover. In the release position, the pump cover releases the pump housing. The pivot bearing arrangement of the known dialysis appliance has two pivot bearings which are arranged spaced apart from each other along the pivot axis, are referred to as pivot joints and each have a first and a second joint portion. The second joint portions are each fastened to the pump housing and, for this purpose, are inserted into blind bores extending perpendicularly to the pivot axis. In order to fasten the pump cover to the pivot joints, a hinge pin is provided which is inserted through a hinge bore, which extends through the pump cover parallel to the pivot axis, and at one end is fastened in a form-fitting manner to a pump cover portion provided for this purpose.

SUMMARY

It is the object of the invention to provide a medical appliance of the type mentioned at the beginning which has a simplified design in comparison to the prior art and in particular permits simplified removal and installation of the cover from and on the housing component.

This object is achieved in that the pivot bearings each have a bearing element and a bearing element receptacle, wherein the bearing elements engage in the respective bearing element receptacle and are pivotable about the pivot axis and linearly movable to a limited extent along the pivot axis, relative to said bearing element receptacle, as a result of which the cover can be shifted in a linearly movable manner along the pivot axis relative to the housing component between a removal position, in which at least one of the bearing elements is not in engagement with the respective bearing element receptacle, and a bearing position, in which the two bearing elements are in engagement with the respective bearing element receptacle, and wherein a spring arrangement is provided by means of which the cover is mounted resiliently along the pivot axis and is elastically pretensioned relative to the housing component in the direction of the bearing position. A simplified design of the medical appliance is achieved by the solution according to the invention. In particular, a significantly simplified removal and installation of the cover in comparison to the prior art is made possible. This is because the limited linear movability of the bearing elements in the bearing element receptacles means that the cover is not merely movable about the pivot axis, but also axially along same to a limited extent. This enables the bearing elements to be disengaged from the respective bearing element receptacle in order to remove the cover. In simplified terms, this is undertaken by a simple lateral linear movement of the cover relative to the pump housing. In order to prevent the bearing elements from being inadvertently disengaged from the respective bearing element receptacle, for example during a pivoting movement of the cover, the spring arrangement is provided. The latter tensions the cover relative to the pump housing in an elastically resilient manner in the direction of the bearing position. By this means, the bearing elements are kept securely in engagement with the respective bearing element receptacle. The cover is mounted resiliently on the housing component along the pivot axis, i.e. axially, by means of the spring arrangement. The pivot bearing arrangement is operatively connected to the cover and to the housing component. In one refinement, the bearing elements are each arranged on the cover and are movable together therewith relative to the housing component. In this case, the bearing element receptacles are arranged on the housing component. Alternatively, the bearing elements can be arranged on the housing component. In this case, the bearing element receptacles are arranged on the cover and are movable together therewith. Furthermore alternatively, one of the bearing elements can be arranged on the cover and a further of the bearing elements on the housing component. In this case, accordingly, one of the bearing element receptacles is arranged on the housing component and a further of the bearing element receptacles on the cover. In one refinement, the bearing elements are formed integrally on the cover and/or on the housing component and therefore form an integral functional portion of the corresponding component. Alternatively, the bearing elements are manufactured as separate components and joined together with the cover and/or the housing component. Furthermore alternatively, one of the bearing elements is formed integrally on the cover and/or on the housing component and a further of the bearing elements is manufactured as a separate component. The same applies analogously in respect of an integral and/or separate formation of the bearing element receptacles. The bearing elements are preferably each configured as a bearing journal, bearing bolt and/or bearing pin. The bearing element receptacles are preferably configured in a complementary manner thereto in each case as a bore in the form of a journal receptacle, bolt receptacle and/or pin receptacle. The bearing elements and the bearing element receptacles interact preferably in a sliding manner. For said axially resilient mounting and pretensioning of the cover by means of the spring arrangement, the latter, in one refinement, has a spring element which is effective between the cover and the housing component. Alternatively, the axially resilient mounting and pretensioning can be brought about by a configuration of the cover, the housing component, at least one of the bearing elements and/or at least one of the bearing element receptacles so as to be spring-elastic at least in portions. The spring-elastic configuration can be achieved here in particular by flexurally elastic material properties and/or by an elastically flexible shaping of the corresponding component. The housing component is preferably a pump housing of a peristaltic pump of the medical appliance. In this case, the cover can also be referred to as a pump cover.

In a refinement of the invention, the spring arrangement has at least one spring element which at one end acts on one of the bearing elements and at the other end is at least indirectly supported on the cover or on the housing component, or the spring arrangement is formed by an elastically dimensionally flexible wall portion of the cover, on which wall portion one of the bearing elements or one of the bearing element receptacles is formed. The spring element spring-elastically counteracts a linear movement of the cover along the pivot axis in the direction of the removal position. In other words, the spring element tensions or presses the cover relative to the housing component in the direction of the bearing position. For this purpose, the spring element acts at one end on the bearing element and at the other end on the cover or the housing component. If the bearing element is arranged on the cover, the spring element acts at the other end on the cover. If the bearing element is arranged on the housing component, the spring element likewise acts at the other end on the housing component. Alternatively, the spring arrangement is formed by said dimensionally flexible wall portion of the cover. When the cover is shifted from the bearing position into the removal position, the wall portion is elastically deformed. The spring force resulting from the elastic deformation counteracts the shifting of the cover into the removal position. The elastic dimensional flexibility of the wall portion can be achieved by a corresponding selection of material and/or configuration of the wall portion. For example, the wall portion can have a comparatively thin wall thickness. Alternatively or additionally, the wall portion can be manufactured from a material which is comparatively flexible in comparison to the remaining components and/or portions of the medical appliance. The corresponding bearing element or the corresponding bearing element receptacle is preferably formed integrally on the dimensionally flexible wall portion.

In a further refinement of the invention, a support arrangement which is operatively connected to the cover and the housing component is provided by means of which the cover can be supported in a form-fitting manner on the housing component counter to a linear movement directed toward the removal position, wherein the support is brought about at least in the covering position, and wherein the support is removed in a defined pivoted position of the cover for removal thereof. The support arrangement counteracts an inadvertent removal of the cover in the covering position and/or during the pivoting about the pivot axis. For this purpose, at least in the covering position, the support arrangement brings about a form fit, which is effective along the pivot axis and is therefore axial, between the cover and the housing component. Said axial form fit is effective in the covering position and blocks an axial linear movement of the cover into the removal position. By contrast, the axial form fit is removed in the defined pivoted position. By this means, the cover can be shifted axially along the pivot axis—and counter to the spring force of the spring arrangement—into the removal position. The support arrangement is preferably formed by functional portions formed integrally on the cover and/or on the housing component. Alternatively or additionally, the support arrangement can have separate components which can be joined together to the cover and/or to the housing component. The support is brought about between axially opposite components and/or portions of the cover and of the housing component.

In a further refinement of the invention, the support arrangement has at least one support element which is arranged on the cover and, at least in the covering position, is supported in a form-fitting manner along the pivot axis on a support portion of the housing component, and which, in the defined pivoted position of the cover, is pivoted away from the support portion about the pivot axis and therefore cannot be supported on said support portion. This permits a structurally particularly simple design of the support arrangement. The support element is preferably formed integrally on the cover. The support is removed preferably exclusively in the defined pivoted position.

In a further refinement of the invention, the defined pivoted position is the release position or a pivoted position of the cover pivoted from the release position further about the pivot axis. The first variant permits the removal of the cover in the release position. By contrast, in the case of the second variant, the removal of the cover is possible not, for example, in the release position, but rather in the pivoted position which is pivoted further. This counteracts an unintended removal of the cover in the release position. Improved use safety can thereby be achieved.

In a further refinement of the invention, the support arrangement has at least one mating support element which is arranged on the cover and, at least in the covering position, is supported in a form-fitting manner along the pivot axis and counter to the support element on a mating support portion of the housing component. By this means, in particular, an improved, namely two-sided, support of the cover in the covering position can be achieved. In a refinement of the invention, the mating support element is also supported on the mating support portion in the release position and/or in the pivoted position, which is pivoted further, of the cover. This provides in particular improved lateral guidance of the cover during the pivoting about the pivot axis. The mating support element is preferably formed integrally on the cover.

In a further refinement of the invention, a holding arrangement which is operatively connected to the cover and to the housing component is provided by means of which the cover is held in the release position counter to a pivoting movement directed into the covering position. The holding arrangement thus prevents the cover from inadvertently pivoting back from the release position into the covering position, for example under the action of gravity. The holding arrangement is preferably formed by functional portions formed integrally on the cover and/or the housing component. Alternatively or additionally, the holding arrangement can have separately manufactured components which are joined together to the cover or to the housing component. The holding arrangement preferably acts in a form-fitting manner in the release position. Alternatively or additionally, the holding arrangement can act in particular magnetically.

In a further refinement of the invention, the holding arrangement has a latching element which is arranged on the housing component and over which a latching portion of the cover can latch by means of a pivoting movement of the cover, wherein the latching portion grips releasably in a form-fitting manner behind the latching element in the covering position. This permits a structurally particularly simple and robust design of the holding arrangement. When the latching element is latched over, the latching portion and the latching element execute an axial relative movement which is therefore directed along the pivot axis. This is in addition to the relative movement resulting from the pivoting movement. In a further refinement of the invention, the latching element and the latching portion are mounted resiliently relative to each other along the pivot axis by means of the spring arrangement. By this means, the function of the holding arrangement is particularly advantageously supported by means of the spring arrangement. The holding arrangement interacts here with the spring arrangement. This is because the latter presses the cover laterally in the direction of the bearing position. By this means, the latching element and the latching portion are mounted axially resiliently against each other indirectly via the spring arrangement. This permits in particular smooth overlatching during the pivoting movement. In addition, the spring arrangement supports the form fit between the latching portion and the latching element.

In a further refinement of the invention, the cover has two side members which are arranged spaced apart from each other along the pivot axis and are angled in relation to a cover top side, wherein the pivot bearings and/or the spring arrangement and/or the support arrangement and/or the holding arrangement are formed integrally at least in sections on at least one of the side members. This refinement of the invention permits a particularly advantageous reduction in the required number of components. A particularly simple design is thereby achieved. In addition, the integral design supports the removal and installation since the components and/or portions which are correspondingly formed integrally are arranged virtually captively on the at least one side member and therefore on the cover. The side members lie axially opposite each other with respect to the pivot axis. In the covering position, the side members engage over the housing component in the lateral direction. In combination with this refinement of the invention, manufacturing the cover in the form of a plastics injection molded component is particularly advantageous.

BRIEF DESCRIPTIONS OF THE DRAWING FIGURES

Further advantages and features of the invention emerge from the description below of a preferred exemplary embodiment of the invention that is illustrated with reference to the drawings.

Figure 2:
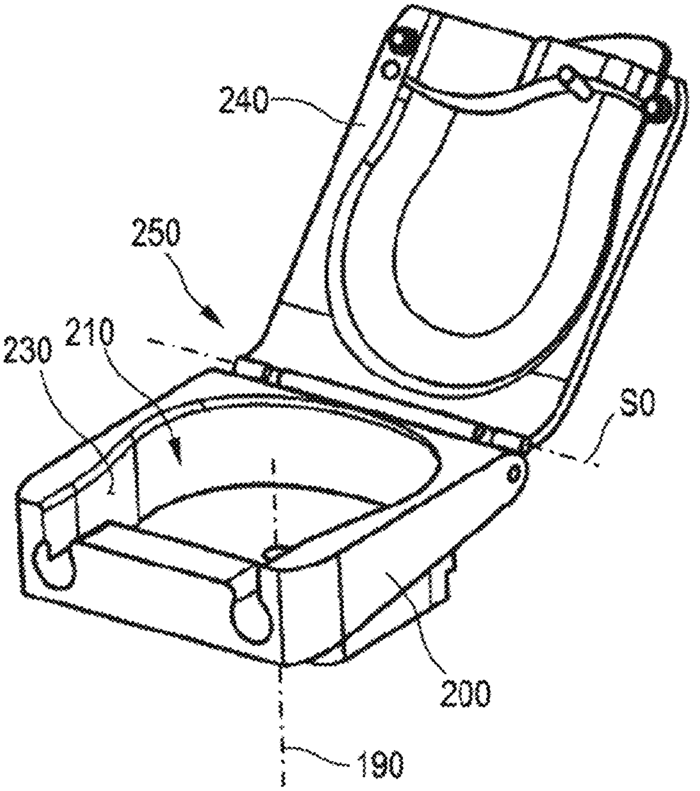
Fig. 2 (Prior Art)
Figure 3:
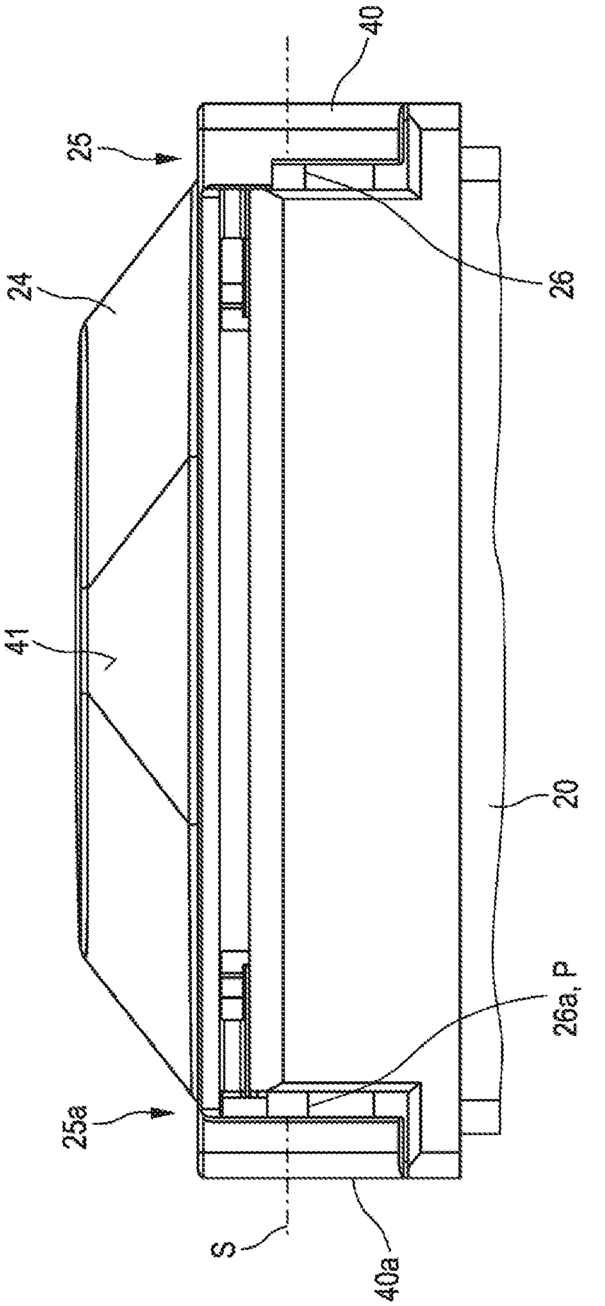
Figure 4:
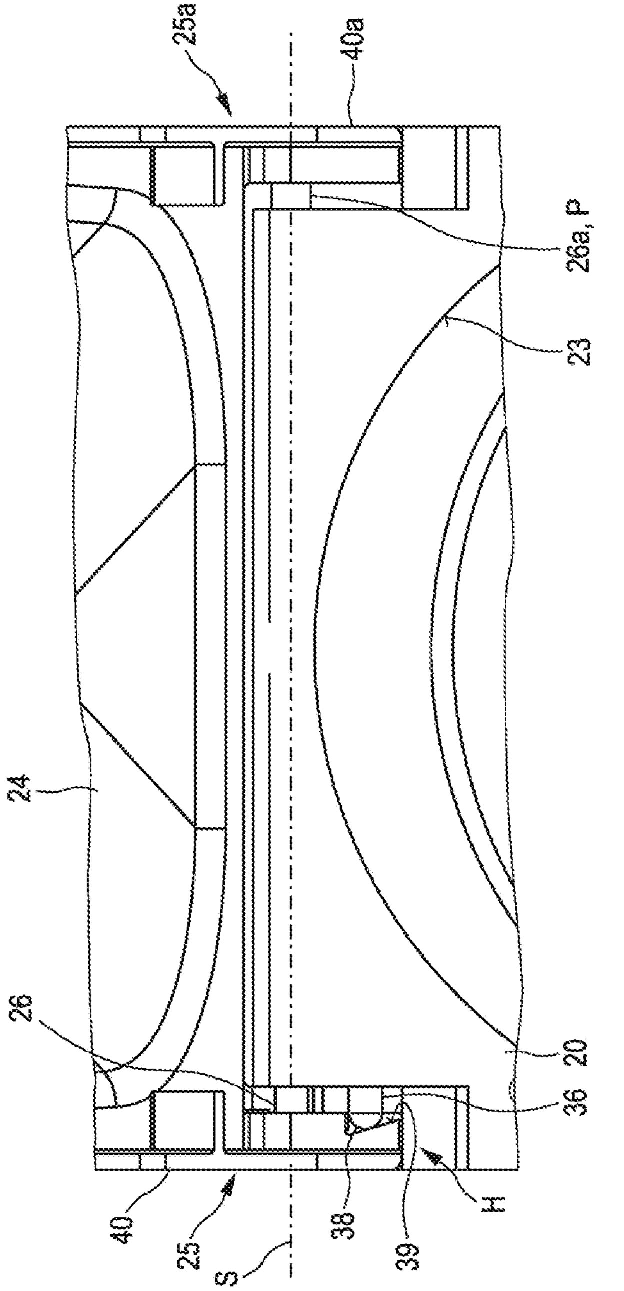
Figure 5:
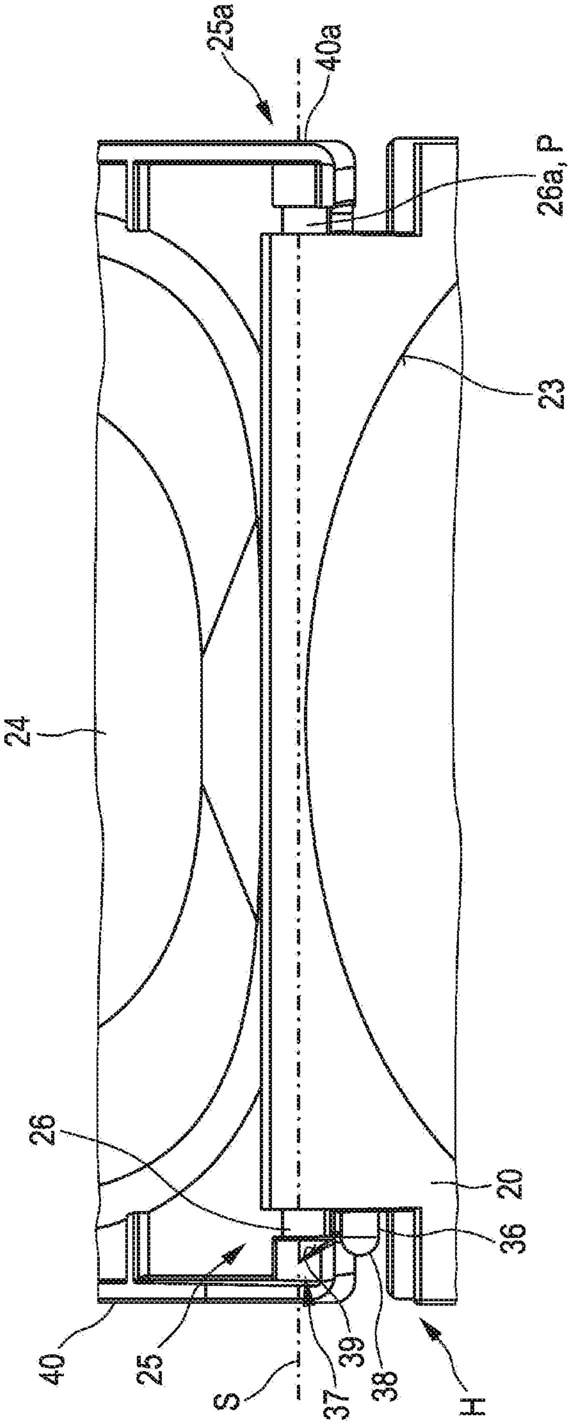
Figure 6:
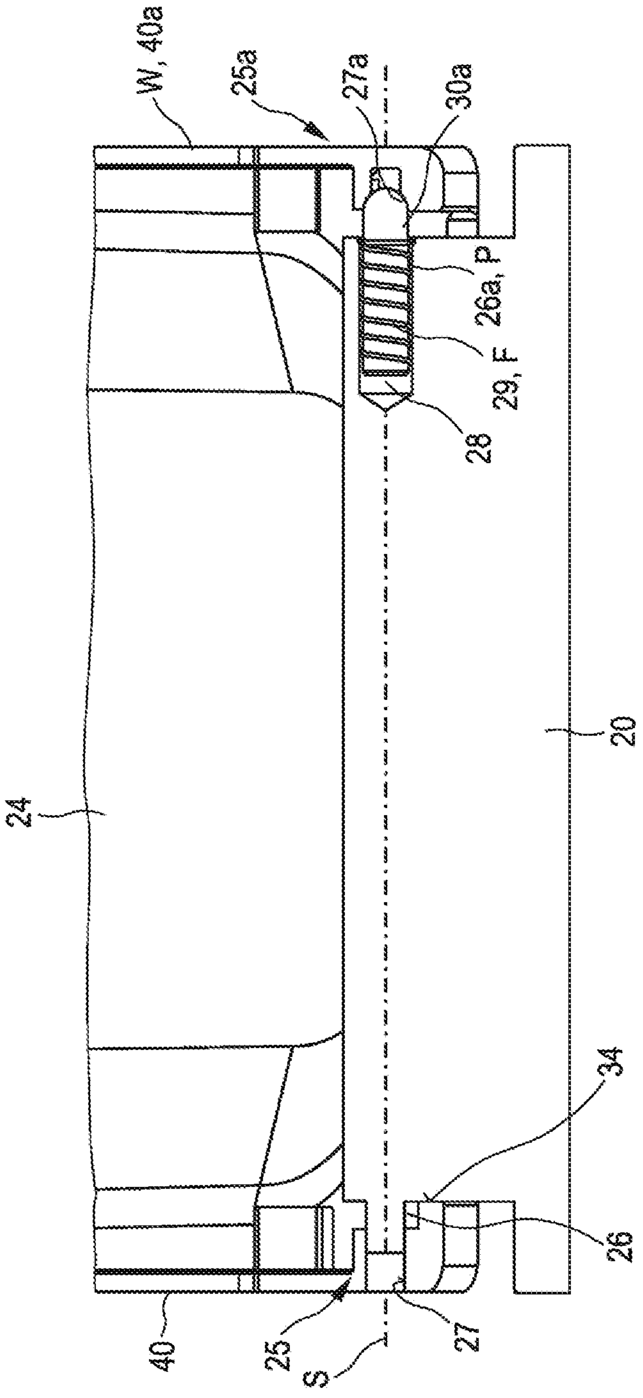
Figure 7:
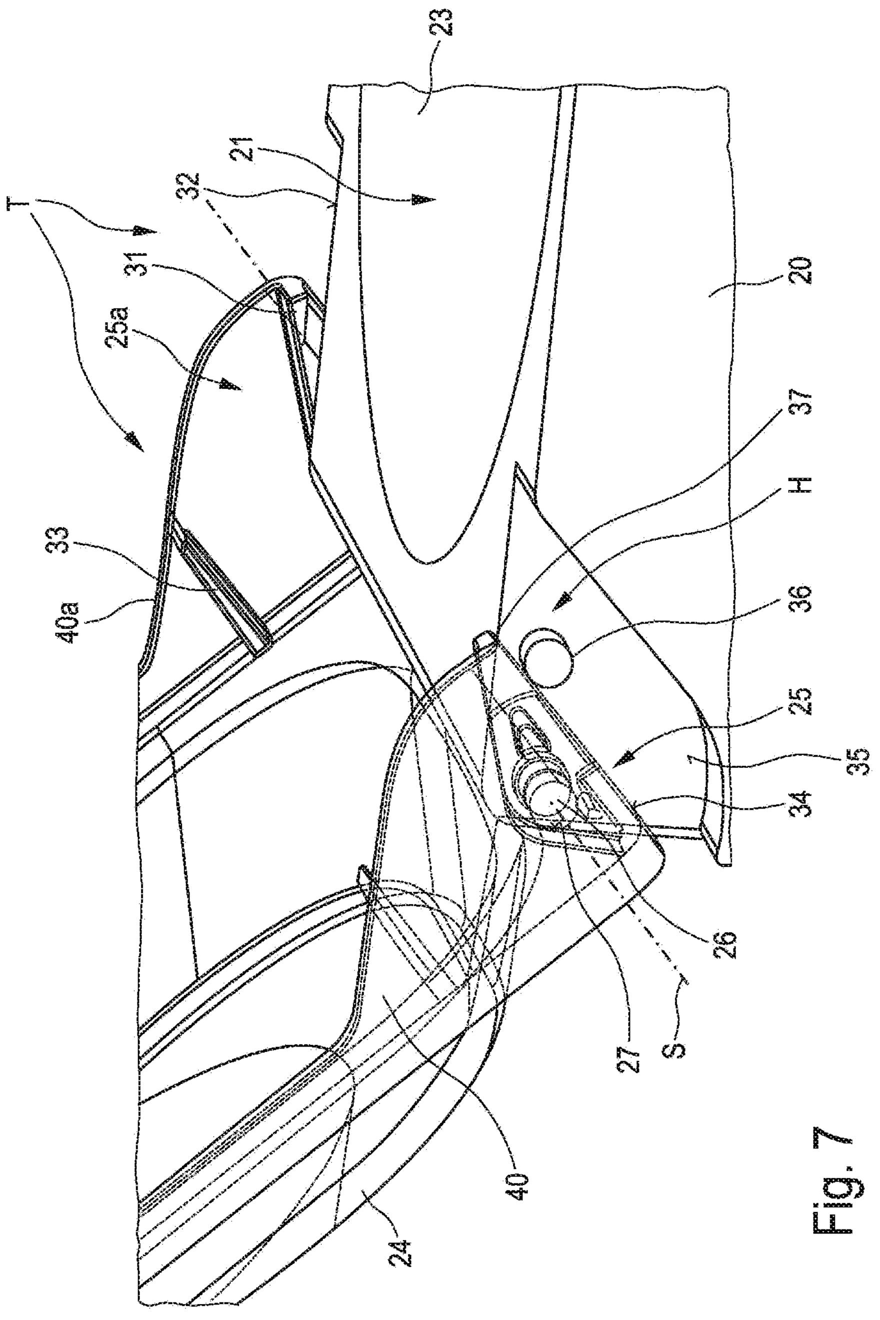

FIG. 1 shows a schematically highly simplified illustration of a cutout of a refinement of a medical appliance according to the invention for extracorporeal blood treatment, with a housing component and a cover, which is blanked out in the drawing, FIG. 2 shows, in a schematic perspective illustration, an arrangement which is known from the prior art, comprising a housing component, a cover and a pivot bearing arrangement for pivoting the cover on the housing component, FIG. 3 shows, in a viewing direction directed from the top downward—with respect to the plane of the drawing of FIG. 1—, the housing component of the appliance according to FIG. 1 with the cover mounted thereon and taking up a covering position, FIG. 4 shows, in a partially sectioned front view—with respect to the plane of the drawing of FIG. 1—, the housing component and the cover in the region of a pivot axis, wherein the cover is pivoted from the covering position according to FIG. 3 in the direction of a release position (FIG. 5), FIG. 5 shows the housing component and the cover in an illustration corresponding to FIG. 4, with the cover taking up the release position, FIG. 6 shows the housing component and the cover in a partial sectional illustration, wherein the intersecting plane runs through the pivot axis, and FIG. 7 shows, in a truncated perspective illustration, the housing component with the cover mounted thereon, with the cover taking up the release position and being illustrated in partially transparent form.

DETAILED DESCRIPTION

FIG. 1 shows sections of a medical appliance V for extracorporeal blood treatment which is configured in the form of a dialysis appliance. FIG. 1 essentially shows an entire extracorporeal circulatory system of the medical appliance V. Said circulatory system has an arterial blood line 1 by means of which blood which is to be treated is guided from a patient (not shown) to a peristaltic pump 2 of the medical appliance V. An arterial pressure sensor 3 is provided upstream of the peristaltic pump 2 with respect to a conveying direction of the blood. The arterial pressure sensor 3 can be used to detect the pressure in the arterial blood line 1 upstream of the peristaltic pump 2. Said pressure may also be referred to as pressure on the low-pressure side. In the conveying direction of the blood downstream of the peristaltic pump 2—and therefore on the high-pressure side—a high-pressure blood line 4 leads to an arterial air trap 5. In the present case, a feed line 6 which is connected to a pump 7 is arranged at an outlet of the peristaltic pump 2. An additive, for example heparin for blood thinning, can be metered in via the feed line 6. Starting from the arterial air trap 5, a line 8 conducts the blood to be treated to a dialyzer 9, to which dialysis fluid is supplied on the input side via a dialysis fluid feed line 10. The blood is treated in the dialyzer 9 in a known manner by means of the dialysis fluid. Used dialysis fluid, which may also be referred to as dialysate, is conducted away from the dialyzer 9 via a dialysis fluid discharge line 11 and fed for disposal or processing (not illustrated). The blood which is to be treated is conducted by means of a blood discharge line 12 from the dialyzer 9 to a venous air trap 13 for separating off air. An air detector/air bubble detector 14 is connected downstream of said air trap and detects whether air which is hazardous for the patient is located in the system. A venous pressure sensor 15, by means of which the venous pressure can be detected, is provided at the venous air trap 13. The treated blood is conducted from the air trap 13 via the air detector/air bubble detector 14 via a venous blood line 16 back to the patient. In addition, a control and monitoring device 17 for controlling and monitoring the medical appliance V is provided. The medical appliance V is encapsulated in a housing G which has a housing front 100 on which in particular the peristaltic pump 2 is mounted.

The peristaltic pump 2 has a rotor 18 and a pump housing 20. The pump housing 20 forms a housing component of the medical appliance V. In a state of the medical appliance V ready for operation, the pump housing 20 is covered by a cover which is yet to be described in more detail and which is mounted pivotably on the pump housing 20 by means of a pivot bearing arrangement, which is likewise yet to be described in detail. Neither the cover nor the pivot bearing arrangement are illustrated in FIG. 1 for graphical reasons.

To clarify the basic design and the functioning of the peristaltic pump 2, reference is first of all made to FIG. 2. FIG. 2 shows a peristaltic pump known from the prior art with a pump housing 200, a cover 240 and a pivot bearing arrangement 250. The pump housing 200 has a receiving recess 210, which may also be referred to as a pump bed. A rotor, not shown with reference to FIG. 2, is accommodated so as to be driven rotatably in the receiving recess 210. The receiving recess 210 is delimited laterally by a support surface 230 which extends arcuately about the rotor axis 190 and is spaced apart radially from the rotor.

The cover 240 is coupled to the pump housing 200 by means of the pivot bearing arrangement 250 so as to be pivotable about a pivot axis S0. The cover 240 takes up an open state in FIG. 2, in which the receiving recess 210 is upwardly released—with respect to the plane of the drawing of FIG. 2. This state may also be referred to as the release position. In a closed state, the cover 240 upwardly covers the receiving recess 210. This state may also be referred to as the covering position.

The basic functioning of the peristaltic pump 2 for pumping the blood between the low-pressure side and the high-pressure side is identical to the functioning of the peristaltic pump according to the prior art that is shown with reference to FIG. 2. To this end, an elastically deformable tube line 22 is arranged in the radial direction between the rotor 18 and the support surface 23 (cf. FIG. 4) of the pump housing 20. The tube line 22 is connected at its opposite ends in a manner known to a person skilled in the art to the arterial blood line 1 and to the high-pressure blood line 4 so as to conduct fluid. In order to pump the blood, the rotating rotor 18 acts on the tube line 22 such that the latter is squeezed together elastically in sections between the rotor 18 and the support surface 23. The resulting squeezing of the tube line 22, which may also be referred to as occlusion, migrates as it were together with the rotating rotor 18 about the rotor axis 19, as a result of which the blood is conveyed from the low-pressure side to the high-pressure side.

In the case of the peristaltic pump known from the prior art according to FIG. 2, the cover 240 is removable and mountable in a comparatively complex manner because of the construction provided there of the pivot bearing arrangement. The configuration according to the invention that is apparent in detail with reference to FIGS. 3 to 7 in particular overcomes this disadvantage.

It is shown there that the cover 24 is mounted pivotably on the pump housing 20 by means of a pivot bearing arrangement 25, 25*a* and so as to be pivotable about a pivot axis S relative to the pump housing 20. In FIG. 3, the cover 24 takes up the covering position. In the latter, the receiving recess 21 of the pump housing 20 is covered by means of the cover 24. From the covering position, the cover 24 can be pivoted about the pivot axis S in the direction of a release position relative to the pump housing 20. In FIGS. 5, 6 and 7, the cover 24 takes up the release position. In the latter, the receiving recess 21 is upwardly released—with respect to the plane of the drawing of FIG. 3. In the operationally ready state shown with reference to FIG. 1, the pump housing 20 and the cover 24 are mounted on the housing front 100 in such a manner that the pivot axis S is extended horizontally in the region of an upper edge (not denoted specifically) of the pump housing 20.

In the embodiment shown, the pivot bearing arrangement 25, 25*a* has two pivot bearings which are arranged spaced apart from each other along the pivot axis S. The pivot bearings of the pivot bearing arrangement 25, 25*a* are also referred to below as first pivot bearing 25 and second pivot bearing 25*a*.

The pivot bearings 25, 25*a* each have a bearing element 26, 26*a* and a bearing element receptacle 27, 27*a*. The bearing elements 26, 26*a* each engage in the axial direction in the respective bearing element receptacle 27, 27*a* and are pivotable about the pivot axis S relative thereto. The bearing elements 26, 26*a* are also referred to below as first bearing element 26 and second bearing element 26*a*. The same applies to the bearing element receptacles 27, 27*a*, which are also referred to as first bearing element receptacle 27 and second bearing element receptacle 27*a*.

It is apparent in particular with reference to FIG. 6 that the bearing elements 26, 26*a* and the bearing element receptacles 27, 27*a* are not merely mounted on one another so as to be pivotable relative to one another about the pivot axis S. On the contrary, at the same time, a linear movability, which is limited in the axial direction of the pivot axis S, between the bearing elements 26, 26*a* and the respective bearing element receptacle 27, 27*a* is ensured.

For this purpose, in the case of the embodiment shown, the second bearing element 26*a* is configured in the form of a bearing pin P and is accommodated axially movably to a limited extent in a receiving bore 28 of the pump housing 20. As a result of this movable accommodating of the bearing pin P, the cover can be moved relative to the pump housing 20 in the lateral direction, i.e. axially along the pivot axis S. The axial position, which can be seen with reference to FIGS. 3 to 7, of the cover 24 with respect to the pump housing 20 may also be referred to as the bearing position. In said bearing position, the two bearing elements 26, 26*a* are in engagement with the respective bearing element receptacle 27, 27*a*. Starting from the bearing position, the cover 24 can be pressed to the left—with respect to the planes of the drawing of FIGS. 4, 5 and 6—until the first bearing element receptacle 27 is disengaged from the first bearing element 26. The cover 24 is then in a removal position. This permits simple manual removal of the cover 24 from the pump housing 20. The same applies analogously to the installation of the cover 24.

In order to prevent inadvertent removal of the cover 24, a spring arrangement 29 is also provided by means of which the cover 24 is mounted resiliently along the pivot axis S and is elastically pretensioned relative to the pump housing 20 in the direction of the bearing position.

In the embodiment shown, the spring arrangement 29 is designed as a spring element F. The spring element F is integrated in the bearing pin P, and therefore the latter may also be referred to as a spring pin P. The spring element F is supported at one end—at any rate indirectly—on the pump housing 20 and acts at the other end on a rear side (not denoted specifically) of a head portion 30*a* of the bearing pin P. The head portion 30*a* engages in the second bearing element receptacle 27*a*.

In the case of an embodiment not illustrated graphically, an alternative refinement of the spring arrangement is provided. In the case of this refinement, the bearing pin P is arranged axially immovably on the pump housing 20, and the resilient mounting and pretensioning in the axial direction is achieved by means of an elastically dimensionally flexible configuration of the cover 24 in the region of a wall portion W. By means of the dimensionally flexible configuration of the wall portion W, the cover can be pressed laterally in the direction of the removal position despite the axially fixed arrangement of the bearing pin P.

In the embodiment shown, the first bearing element 26 is configured as a bearing journal. Accordingly, the first bearing element receptacle 27*a* is designed as a journal receptacle.

Furthermore, it is apparent in particular with reference to FIG. 6 that the bearing element receptacles 27, 27*a* are each formed integrally on the cover 24. By contrast, the bearing elements 26, 26*a* are arranged on the pump housing 20, the first bearing element 26 being formed integrally on the pump housing 20. For this purpose, by contrast, the second bearing element 26*a* or the bearing pin P is manufactured as a separate component and joined together with the pump housing 20 by insertion into the receiving bore 28.

In order to prevent the cover 24 from being unintentionally removed from the pump housing 20, in the embodiment shown a support arrangement T which is formed between the cover 24 and the housing component 20 is provided (FIG. 7). By means of the support arrangement T, the cover 24 can be supported in a form-fitting manner on the pump housing 20 counter to a linear movement directed into the removal position. In the present case, this support is brought about here at least in the covering position. By contrast, the support is removed in a defined pivoted position (FIG. 7), as a result of which the cover 24—as it lacks a form-fitting lateral support on the pump housing 20—can be displaced from the bearing position into the removal position.

In the embodiment shown, said defined pivoted position of the cover 24 is the release position. In the case of an embodiment that is not shown, the defined pivoted position for removing the cover 24 is a pivoted position of the cover 24 pivoted further about the pivot axis S from the release position.

The support arrangement here has a support element 31 which is arranged on the cover 24 and, for support, interacts in a form-fitting manner with a support portion 32 arranged on the pump housing 20. The support portion 32 is formed by a lateral outer surface of the pump housing 20. The support element 31 is integrally formed here on the cover 24 and is opposite the support portion 32 in the axial direction of the pivot axis S. This is at any rate in the covering position. In the release position shown with reference to FIG. 7, the support element 31 is pivoted away from the support portion 32 about the pivot axis S together with the cover 24 and therefore cannot be supported axially on said support portion 32. In other words, the support element 31 blocks the axial movability of the cover 24 at least in the covering position in such a manner that the cover 24 is not displaceable from the bearing position into the removal position. Even in the event of a pivoting movement of the cover 24 from the covering position, the support element 31 remains positioned axially in relation to the support portion 32 such that the axial movability of the cover is then also blocked. Only in the defined pivoted position of the cover 24, here the release position, is the support element 31 no longer positioned in relation to the support portion 32 such that the axial movability of the cover is released in the direction of the removal position.

In the embodiment shown, the support arrangement T also has a further support element 33. The support element 33 ensures as flat a support as possible on the support portion 32 in particular in the covering position.

Furthermore, the support arrangement T here has a mating support element 34 (FIGS. 6 and 7) which is arranged on the cover and, at any rate in the covering position, is supported on the pump housing 20 axially and counter to the support element 32. For this purpose, the pump housing 20 has a mating support portion 35. The mating support portion 35 is formed in a manner corresponding to the support portion 32 by a lateral surface of the pump housing 20. The mating support element 34 and the mating support portion 35 lie opposite each other in the axial direction of the pivot axis S and counteract an axial movement of the cover 24 directed from the left to the right—with respect to the plane of the drawing of FIG. 6. This prevents in particular an inadvertent disengaging of the bearing pin P from the second bearing element receptacle 27*a*. In the embodiment shown, the mating support element 34 is positioned in relation to the mating support portion 35 over the entire pivoting range of the cover 24 in the axial direction. In other words, the cover 24 can be supported on the mating support portion 35 by means of the mating support element 34 not merely in the covering position, but also in all further pivoted positions.

With respect to FIG. 1, the cover 24 protrudes upward obliquely forward from the pump housing 20 in the release position. In order to hold the cover 24 in the release position counter to the action of gravity, a holding arrangement H is provided here. The holding arrangement H holds the cover in the release position counter to a pivoting movement directed into the covering position. The holding arrangement H is formed between the cover 24 and the pump housing 20. The holding arrangement H here has a latching element 36 arranged on the pump housing 20 and a latching portion 37 formed on the cover 24. The latching element 36 protrudes laterally from the pump housing 20 in the axial direction of the pivot axis S and is arranged here in the region of the mating support portion 35. The latching element 36 is provided with a rounded latching contour 38 on an outer end region. The latching portion 37 is formed integrally on the cover 24 and has a beveled latching contour 39 (FIG. 4). The latching portion 37 can latch over the latching element 36 by means of a pivoting movement of the cover 24. In this case, first of all the beveled latching contour 39 passes into sliding contact with the rounded latching contour 38 of the latching element 36. This is shown in FIG. 4. The latching portion 37 is pressed here outwardly in the axial direction relative to the latching element 36. After latching over the latching element, the latching portion 37 grips behind the rounded latching contour 38 such that the cover 24 is held in a form-fitting manner in the release position.

When the latching element 36 is overlatched, the holding arrangement H interacts in an advantageous manner with the spring arrangement 29. This is because the previously described axial yielding movement of the latching portion 37 and therefore of the entire cover 24 is assisted by the resilient mounting of the bearing pin P. The previously described overlatching thereby takes place particularly smoothly and with little wear. At the same time, the resilient mounting or the pretensioning by means of the spring arrangement 29 assists the secure gripping-behind action of the latching element 36.

Furthermore, the cover 24 here has two side members 40, 40*a* which are arranged spaced apart from each other along the pivot axis S and may also be referred to as first side member 40 and second side member 40*a*. The side members 40, 40*a* are angled in relation to a cover top side 41 of the cover 24, with an angle of approximately 90° being provided here. The side members 40, 40*a* engage laterally over the pump housing 20 in the covering position. The side members 40, 40*a* are arranged lying axially opposite the mating support portion 35 or the support portion 32 of the pump housing 20 here.

The bearing element receptacles 27, 27*a* are formed here in the region of the side members 40, 40*a*. In more precise terms, the first bearing element receptacle 27 is formed on the first side member 40. In the present case, the bearing element receptacle 27 is extended here in the form of a through bore through the first side member 40. The second bearing element receptacle 27*a* is formed in the region of the second side member 40*a*.

In addition, the support arrangement T is also formed here at least in sections in the region of the side members 40, 40*a* (FIG. 7). The support element 31 and the further support element 33 are formed on an inner-lying inner side of the second side member 40*a*. The mating support element 34 is formed on an inner side of the first side member 40 opposite the inner side of the second side member 40*a*.

In addition, the holding arrangement H is also formed at least in sections in the region of the side members 40, 40*a*. In more precise terms, the latching portion 37 is formed on the inner side of the first side member 40.

The previously described, preferably integral, design of the corresponding functional portions of the pivot bearing arrangement 25, 25*a*, the support arrangement T and the holding arrangement H on the side members 40, 40*a*, in particular the inner sides thereof, is particularly advantageous. In the embodiment shown, the cover 24 is manufactured as a plastics injection molded component.

The invention claimed is:

1. A medical appliance for extracorporeal blood treatment comprising:

a housing component;

a cover comprising a top side;

a pivot bearing arrangement by which the cover is mounted on the housing component so as to be pivotable about a pivot axis relative to the housing component; and a spring arrangement, the cover being pivotable at least between a covering position, in which the cover covers the housing component, and a release position, in which the cover releases the housing component, the pivot bearing arrangement comprising at least a first pivot bearing and a second pivot bearing spaced apart from the first pivot bearing along the pivot axis, the first pivot bearing comprising a first bearing element and a first bearing element receptacle, the second pivot bearing comprising a second bearing element and a second bearing element receptacle, the first bearing element engaging in the first bearing element receptacle, the second bearing element engaging in the second bearing element receptacle, the first bearing element and the second bearing element being pivotable about the pivot axis and linearly movable to a limited extent along the pivot axis relative to the first bearing element receptacle and the second bearing element receptacle, respectively, as a result of which the top side of the cover is configured to be shifted in a linearly movable manner along the pivot axis relative to the housing component between a removal position, in which at least one of the first bearing element and the second bearing element is disengaged from at least one of the first bearing element receptacle and the second bearing element receptacle, respectively, and a bearing position, in which the first bearing element and the second bearing element are engaged with the first bearing element receptacle and the second bearing element receptacle, respectively, the first bearing element, the first bearing element receptacle, the second bearing element, and the second bearing element receptacle each having a longitudinal axis that is coaxial with the pivot axis, the longitudinal axes of the first bearing element, the first bearing element receptacle, the second bearing element, and the second bearing element receptacle remaining coaxial with one another and with the pivot axis as the top side of the cover is shifted between the removal position and the bearing position, the cover being mounted resiliently to the housing component along the pivot axis by the spring arrangement and elastically pretensioned relative to the housing component in a direction of the bearing position by the spring arrangement.

2. The medical appliance according to claim 1, wherein:

the spring arrangement has at least one spring element comprising a first end that acts on one of the first bearing element and the second bearing element, the at least one spring element comprising a second end that is at least indirectly supported on the cover or the housing component, or the spring arrangement is formed a wall portion of the cover, the wall portion being elastically dimensionally flexible, on which wall portion one of the first bearing element and the second bearing element or one of the first bearing element receptacle and the second bearing element receptacle is formed.

3. The medical appliance according to claim 1, further comprising support surfaces operatively connected to the cover and to the housing component, the cover being supportable by the support surfaces in a form-fitting manner on the housing component counter to a linear movement directed toward the removal position, wherein the cover is supported by the support surfaces at least in the covering position, and wherein the support is removed in a defined pivoted position of the cover for removal of the cover.

4. The medical appliance according to claim 3, wherein the support surfaces comprise at least one first surface arranged on the cover and, at least in the covering position, is supported in a form-fitting manner along the pivot axis on a at least one second surface of the housing component, and which, in the defined pivoted position of the cover, is pivoted away from the at least one second surface about the pivot axis and therefore cannot be supported on said at least one second surface.

5. The medical appliance according to claim 3, wherein the defined pivoted position of the cover is a release position or a pivoted position of the cover pivoted from the release position further about the pivot axis.

6. The medical appliance according to claim 3, wherein the support surfaces comprise at least one first mating surface which is arranged on the cover and, at least in the covering position, is supported in a form-fitting manner along the pivot axis and counter to at least one second mating surface of the housing component.

7. The medical appliance according to claim 1, further comprising a first latch surface operatively connected to the cover and a second latch surface operatively connected to the housing component, wherein the cover is held in the release position counter to a pivoting movement directed into the covering position by an engagement between the first latch surface and the second latch surface.

8. The medical appliance according to claim 7, wherein the second latch surface is latchable over the first latch surface by a pivoting movement of the cover, and wherein the second latch surface grips releasably behind the first latch surface in the covering position in a form-fitting manner.

9. The medical appliance according to claim 8, wherein the first latch surface and the second latch surface are mounted resiliently relative to each other along the pivot axis by the spring arrangement.

10. The medical appliance according to claim 1, wherein:

the cover has a first side member and a second side member that are spaced apart from each other along the pivot axis and are angled in relation to the top side, the first side member is angled relative to the cover top side by a first angle, the second side member is angled relative to the cover top side by a second angle, and the first angle and the second angle remain fixed as the cover is shifted between the removal position and the bearing position.

* * * * *